United States Patent
Naghavi

(10) Patent No.: US 7,077,812 B2
(45) Date of Patent: Jul. 18, 2006

(54) APPARATUS AND METHOD FOR PALPOGRAPHIC CHARACTERIZATION OF VULNERABLE PLAQUE AND OTHER BIOLOGICAL TISSUE

(75) Inventor: Morteza Naghavi, Houston, TX (US)

(73) Assignee: The Board Regents of the University System, Austin, TX (US)

( * ) Notice: Subject to any disclaimer, the term of this patent is extended or adjusted under 35 U.S.C. 154(b) by 0 days.

(21) Appl. No.: 10/302,748

(22) Filed: Nov. 22, 2002

(65) Prior Publication Data
US 2004/0102722 A1 May 27, 2004

(51) Int. Cl.
*A61B 5/117* (2006.01)
*A61B 5/103* (2006.01)

(52) U.S. Cl. .................................... 600/587
(58) Field of Classification Search ............... 600/549, 600/309, 374, 368, 509, 474; 128/898, 899; 606/41; 607/101, 133, 122
See application file for complete search history.

(56) References Cited

U.S. PATENT DOCUMENTS

| | | | |
|---|---|---|---|
| 5,421,328 A * | 6/1995 | Bedingham | 600/309 |
| 5,871,449 A * | 2/1999 | Brown | 600/474 |
| 6,092,528 A * | 7/2000 | Edwards | 128/898 |
| 6,615,071 B1 | 9/2003 | Casscells, III et al. | |
| 6,748,255 B1 * | 6/2004 | Fuimaono et al. | 600/374 |
| 2002/0111560 A1 * | 8/2002 | Kokate et al. | 600/549 |

* cited by examiner

*Primary Examiner*—Max F. Hindenburg
*Assistant Examiner*—Brian Szmal
(74) *Attorney, Agent, or Firm*—Duane Morris LLP

(57) ABSTRACT

The present invention discloses a device and methods for characterizing vulnerable plaque and cancer tissue by measuring changes in tissue elasticity compared to that of normal tissue. The system includes a catheter with an expandable element at a proximal end. The expandable element is equipped with pressure sensors to detect changes in tissue elasticity and can be additionally equipped with sensors that detect tissue temperature and pH. For arterial tissue or tissue lining a body cavity, the device can also be equipped with width gauges that measure the diameter of the artery lumen or the width of any section of the body cavity. The distal end of the catheter may be attached to a motorized pullback device connected to a computer. Data collected by the device sensors are sent to the computer for processing and analysis.

61 Claims, 3 Drawing Sheets

APPARATUS AND METHOD FOR PALPOGRAPHIC CHARACTERIZATION OF VULNERABLE PLAQUE AND OTHER BIOLOGICAL TISSUE

BACKGROUND OF THE INVENTION

1. Field of the Invention

The present invention relates generally to the field of medical device. More specifically, the present invention relates to a device that employs palpography technology to characterize vulnerable plaque and other biological tissue such as cancer tissue.

2. Description of the Related Art

Atherosclerosis, a process underlying coronary artery disease, myocardial infarction and cerebrovascular disease, is a leading cause of morbidity and mortality in industrialized countries. The atherosclerotic plaque is often indolent and progressive and may destabilize without warning. This is defined as progressing from a pre-plaque to a vulnerable plaque. Cellular and molecular characteristics and the structure of the atherosclerotic plaque determine its vulnerability to rupture. Imaging techniques currently available utilize invasive and non-invasive methods to characterize coronary artery stenosis.

Current technique for vulnerable plaque detection may include combinations of thermography, NIR (near infrared) spectrum imaging, IVUS (intravascular ultrasound) imaging, nuclear labeling, chemical coding, micro-coil MRI, focal ELISA, and measurement of C-reactive protein, oxidized chemicals, lactate or pH. Detection, however, usually occurs late in the course of disease after symptoms have presented. Through early detection and a targeted treatment strategy, it is hoped that the burden of ischemic heart disease can be reduced. (Fischer et al., 2000; Naghavi et al. 2001).

Vulnerable atherosclerotic plaques are known to be inflamed and have higher temperature than the adjacent areas. A thermography catheter with an expandable basket having 4 to 8 expandable basket members, each of which was equipped with two thermocouples have been developed. It was reported that temperature heterogeneity was detected in five in-bred atherosclerotic dogs and ten Watanabe rabbits. A thermo-elastography system provides thermal, structure and elasticity data for detection of plaques and determination of their functional status (Gul et al., 2001).

Hence, inflamed vulnerable atherosclerotic plaques can be detected based on their increased temperature. An infrared angio-thermography catheter for imaging the thermal characteristics of arterial walls has been reported. The system has a thermal resolution of 0.01° C. and spatial resolution of 100 microns. It was reported that a side-viewing thermography using a 4 French infrared fiber optic bundle catheter is feasible. A realtime imaging reconstruction software continuously records the linear images obtained through the 1 mm window and processes them into two-dimensional and virtual longitudinal color-coded thermographic images of the lumen (Naghavi et al., 2001).

Plaque hypoxia and ischemia have been identified and correlated for a long time. Activated macrophages, in particular those incubated with Ox-LDL, produce enormous amounts of lactate and reduce their environmental pH to acidic levels. Near infrared spectroscopy is one of the few available non-destructive techniques for in vivo measurement of tissue pH. A near-infrared fiber optic catheter with the capability to measure reflectance spectra from the vessel wall has been developed to study the spectroscopic characteristics of lactate and pH in human carotid atherosclerotic plaques. The catheter has the capability to image lactate and pH distribution in the plaque with the help of a specialized software program (Khan et al., 2001).

Human carotid endarterectomized plaque, atherosclerotic rabbit aorta, and ApoE-deficient mice aorta show marked temperature heterogeneity due to inflammation in contrast to normal arterial wall. Plaque temperature and pH are inversely correlated, suggesting that hot plaques are acidic. Plaques with a large lipid core, macrophage infiltration, and no calcification (vulnerable plaques) have lower pH than calcified and fibrotic (stable) plaques (Naghavi et al., 2002).

There are currently several feasible and accurate methods to study the arterial wall morphology like angiography and intravascular ultrasounds. Diamantopoulos et al. developed a 3F intracoronary catheter that can slide over a conventional angioplasty guidewire. This catheter is equipped with an array of electrically isolated ultra-thin metallic film rings using the capacitometry principles. It was reported that the plaque morphology is well correlated with the images acquired by IVUS. The method can distinguish calcified areas, areas with fatty content and other tissues for in vivo assessment of a vulnerable plaque (Diamantopoulos et al., 2001).

Simultaneous thermal and morphology mapping of the coronary arteries in vivo have been reported by using a catheter system combining intravascular ultrasound and multi-point thermography at the same time and position. The system includes a 3.5F catheter using 4 thermisters to study the temperature at 360° of the arterial wall, and an ultrasound scanning system for the simultaneous acquisition of intravascular images. The 2D plots and 3D re-constructions are automatically provided from a study of 10 non-atherosclerotic rabbits (Diamantopoulos et al., 2001).

Plaque temperature has been associated with plaque vulnerability. A new insight into plaque vulnerability by means of thermography and advanced computer algorithms has been reported. A new catheter-based system that has the capability of simultaneous intravascular echogram and temperature sampling at the same location is used in 5 atherosclerotic rabbits. A 3-D color-coded thermal mapping of the atherosclerotic plaque verified the existence of temperature heterogeneity inside the individual plaques (Diamantopoulos et al., 2001).

Known vulnerable plaques are more likely to be soft plaques. In contrast, stable plaques are likely to be fibrotic and calcified (hard plaque). The present invention discloses a method and apparatus for screening hot and soft plaques to identify vulnerable plaques. This system is designated as thermo-elastography catheter and may be superior and more cost-effective compared to an intravascular sono-elastography described by Cespedes and de Korte (de Korte et al., 2002 Mar; de Korte et al., 2002 April) or a combination of thermosensors and IVUS elastography currently investigated by Serruys and Diamontapolos.

The prior art offers means to characterize arterial walls and atherosclerotic plaques including the use of thermo-elastography, sono-elastography and near infrared spectroscopy techniques. The present invention provides a diagnostic device for studying tissue environments, including tissue environments enclosing a body lumen. In particular, the present invention further provides a device that enhances the technology of prior art to detect and diagnose atherosclerotic plaques; thereby, fulfilling a long standing need and desire in the art.

SUMMARY OF THE INVENTION

The invention discloses a device that can be used to characterize biological tissue such as vulnerable plaque and cancer tissue by determining tissue elasticity and texture. Tissue elasticity is determined by means of sensors that detect pressure differentials in a tissue. The devices comprises a catheter with a proximal end that has an expandable element carrying pressure sensors and a distal end connected to a motorized system through a guide wire that runs the length of the catheter shaft. The expandable element can further comprise one or more temperature and pH sensors. The shaft of the catheter carries one or more width gauges for measuring width, specifically the diameter of an artery lumen. The motorized system is further connected to a computer which processes and analyzes data input from the sensors on the expandable element and on the shaft.

In a preferred embodiment, the expandable element of the catheter has a plurality of wires in a basket-shaped arrangement. The basket arrangement has attached to it a number of pressure sensors. The basket arrangement can also have additional sensors for temperature and pH attached to it.

In another preferred embodiment, the expandable element of the catheter has a plurality of wires in a radial arrangement. The expandable element on this second embodiment may also be loaded with temperature and pH sensors.

Data from the sensors on the catheter of both preferred embodiments can provide a radial as well as longitudinal elasticity, texture, temperature and pH map of the tissue wall of an artery or a body cavity after analysis by the computer via a software reconstruction program.

One object of the present invention discloses a method to characterize atherosclerotic tissue in an artery of a patient using the preferred embodiments of the device disclosed. Measurements taken by the device is analyzed and compared to those taken from tissue free of atherosclerotic plaque.

Yet another object of the invention discloses a method for screening biological tissue for cancer during an interventional procedure such as a biopsy using the preferred embodiments of the device disclosed. Measurements taken by the device is analyzed and compared to those taken from tissue free of cancer.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 2B shows an expandable intravascular basket catheter with a pressure sensor and a temperature sensor. The pressure sensor serves as a feedback to ensure contact with tissue wall for temperature measurements.

DETAILED DESCRIPTION OF THE INVENTION

The invention discloses a medical device that can be used to characterize biological tissue such as vulnerable plaque and cancer tissue by determining tissue elasticity and texture. Tissue elasticity is determined by means of pressure sensors that detect pressure differentials within a tissue. The device comprises a catheter with a proximal end and a distal end, a shaft traversing the catheter and an expandable element at the proximal end. A guide wire within the shaft is configured and adapted for moving the catheter in longitudinal and circumferential directions. The expandable element carryies at least one pressure sensor. The distal end of the catheter is connected to a motorized system for deployment and pullback of the catheter. The expandable element is expandable during deployment of the catheter and retractable during insertion of the catheter.

Tissue stiffness is determined in terms of differential pressures expressed as an elasticity index. Elasticity index is defined as a ratio of Young's moduli of the tissue to a reference tissue at a predetermined pressure. The pressure sensor on the catheter can be a silicone membrane sensor, an ultrasound sensor or a force gauge sensor. Where the sensor is an ultrasound sensor, the sensor comprises an ultrasound system that emits and receives ultrasound signals. Pressure sensors on the expandable element measure pressure differentials simultaneously as the expandable element expands to make contact with tissue wall. The expandable element can also have additional temperature and pH sensors for determining tissue temperature and pH. The temperature sensor can be a thermocouple sensor, a thermister sensor or an infrared sensor, which comprises an optical fiber. Further, the pressure sensors serve as a feedback to ensure tissue wall contact for temperature measurements. Also, the catheter shaft has additional sensors to measure temperature, pressure and pH and at least one width gauge for measuring width, such as the diameter of an artery lumen.

Figure 1:
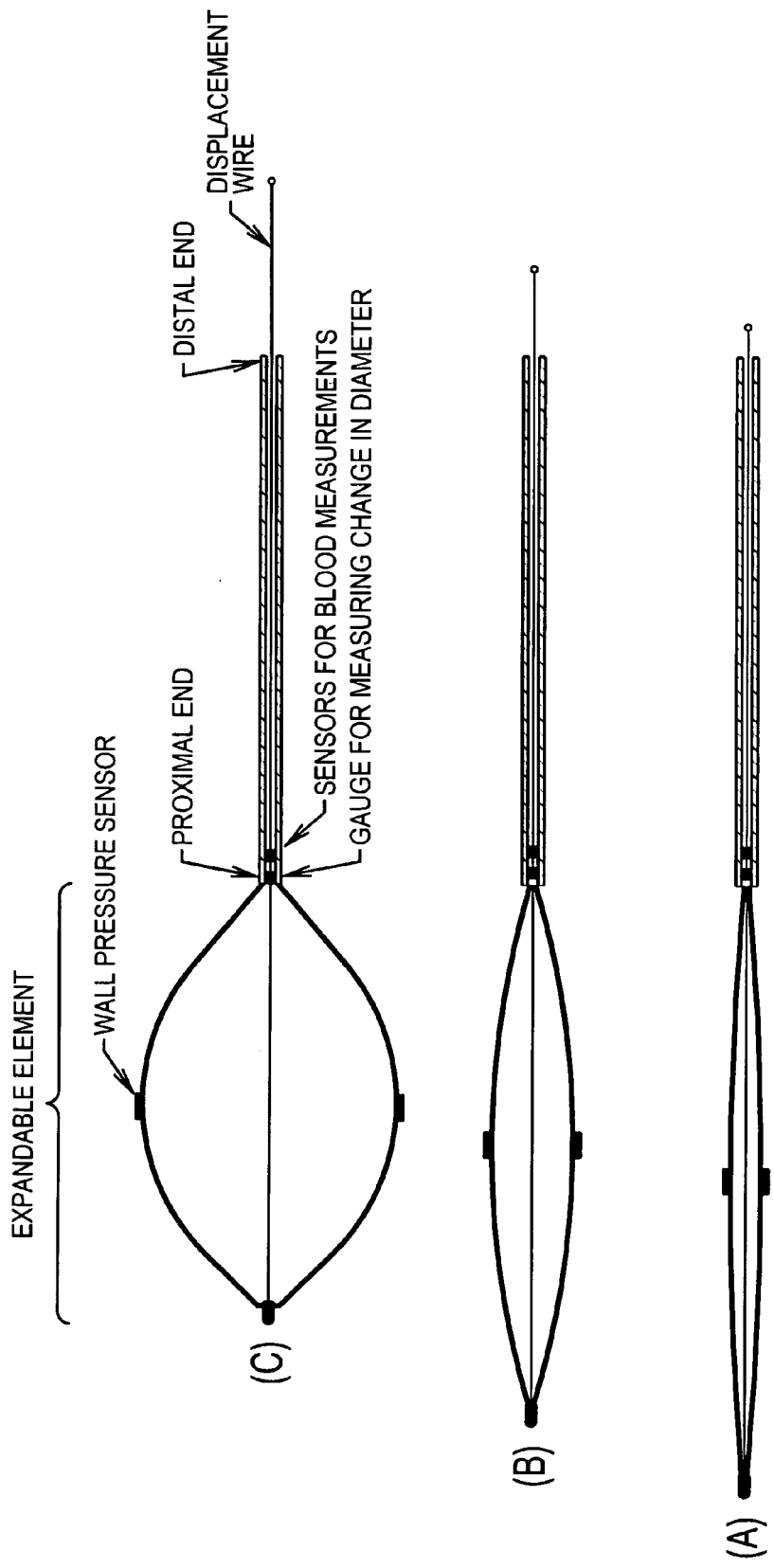
FIG. 1 shows an intravascular expandable basket catheter for monitoring pressure differentials or both pressure and temperature differentials of vulnerable plaque to characterize it by stiffness and texture. The catheter can also be equipped with pH sensors. The figure shows the catheter in a retracted position (FIG. 1A), an intermediate position (FIG. 1B) and an expanded position (FIG. 1C). The catheter is shown with the pressure sensor on the expandable element and the shaft running through its proximal and distal ends. Width gauges are attached to the shaft for measuring diameter change of an artery. In addition, shaft sensors for measuring blood temperature, pressure and pH are shown. A displacement wire within the shaft is adapted to take measurements when the catheter is fully expanded.
Figure 2A:
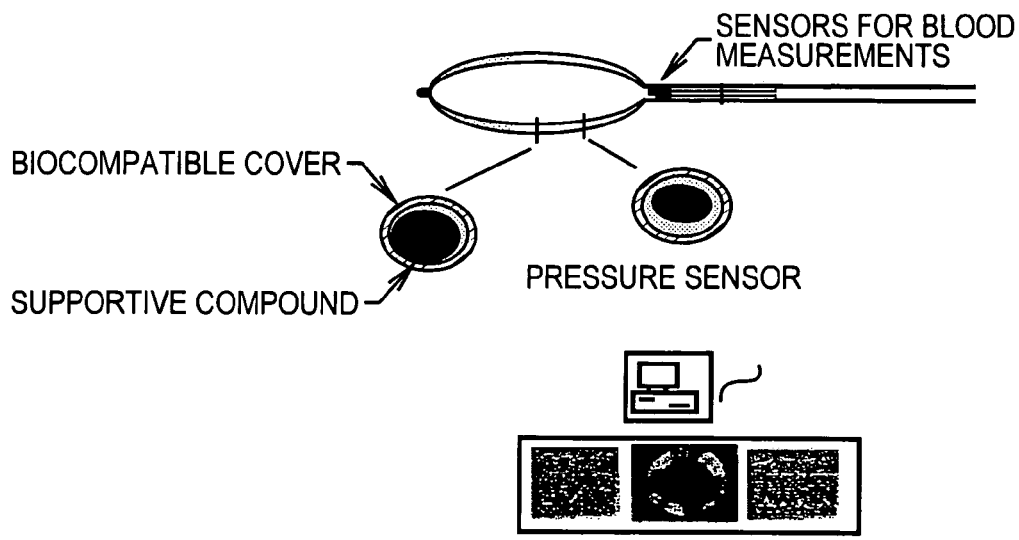
FIGS. 2A and 2B shows an expandable intravascular basket catheter with a pressure sensor. Additional sensors shown on the shaft take measurements of pressure, temperature and pH of the blood.
Figure 2B:
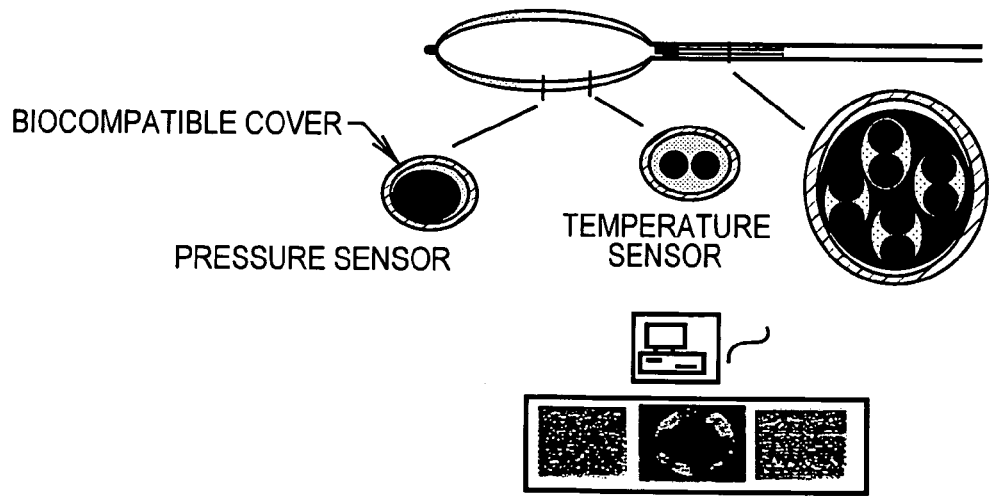

In a preferred embodiment, the expandable element on the catheter comprises a plurality of wires in a basket arrangement (FIGS. 1, 2A and 2B). The pressure sensors so attached to the basket arrangement of wires can be cantilever sensors.

Figure 3:
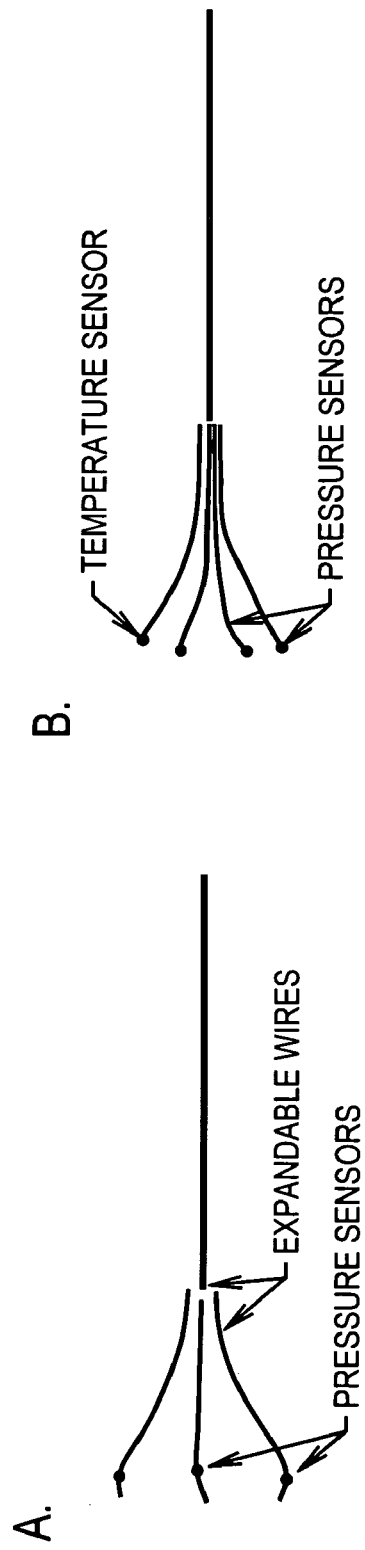
FIGS. 3A and 3B show alternative designs for palpography catheters. Each design is equipped with a plurality of wires on which are attached pressure sensors or a combination of pressure and temperature sensors. Additional width gauges can also be attached

In a second preferred embodiment, the expandable element on the catheter comprises a plurality of wires in a radial arrangement (FIGS. 3A and 3B). Similarly, the pressure sensors attached to the radial arrangement of wires can be cantilever sensors.

Data from the device and its preferred embodiments are inputted to a computer which connects to and controls the motorized system attached to the distal end of the device. The data is analyzed by the computer via a software reconstruction program which creates three-dimensional image maps of the tissue wall.

Rupture of atherosclerotic plaque causes acute myocardial infarction and unstable angina, disease processes that affect about 2.5 million Americans each year and result in about 500,000 deaths. Plaque rupture is caused by progressive degradation of the thin (fibrous or non-fibrous) cap that separates the atherosclerotic plaque contents from the flowing blood in the lumen of an artery. As the thin cap gets progressively degraded (possibly involving erosion or stress), it thins and ultimately ruptures, thereby allowing blood to enter the plaque, an event which stimulates blood clot at the site of rupture that obstruct blood flow.

It has now been accepted that atherosclerotic coronary artery plaque fissure, rupture, or erosion leads to acute coronary syndromes. Pathologic studies have unequivocally shown that vulnerable arterial plaque has less collagen, an increase in lipid pool constituency, and diminished smooth muscle cells. However, vulnerable arterial plaque has a relatively high mononuclear cell count of monocytes and macrophages (Wang et al., 1994). Furthermore, the extracted tissue from vulnerable plaque is rich in interleukin-6, tumor necrosis factor alpha, and gamma interferon. These studies strongly correlate the presence of inflammation in affected coronary arteries with vulnerable plaque at risk of rupture.

Inflammation of a diseased coronary artery sets up the potential for embolization, the latter sequel in patients with ischemic heart disease. The frequency and importance of embolization were examined using emboli entrapment devices during percutaneous coronary intervention, along with new imaging modalities including myocardial contrast echocardiography, Doppler, magnetic resonance imaging, and nuclear scintigraphy. Embolization can occur spontaneously in inflamed coronary arteries or iatrogenically via intracoronary manipulation with catheters. The importance of embolization into the microvasculature relates to the potential for microvascular obstruction that leads to cell death.

Falk et al. (1995) disclosed various aspects of coronary plaque disruption and the vulnerability of plaques. Plaque disruption occurs most frequently where the cap is thinnest, most heavily infiltrated by foam cells, and therefore weakest. For eccentric plaques, the rupture often occurred at the shoulder region of the plaque, which is the junction between the plaque and the adjacent less-diseased vessel wall. Pathoanatomic examination of intact and disrupted plaques and in vitro mechanical testing of isolated thin caps from aorta indicate that vulnerability to rupture depends on (1) size and consistency of the atheromatous core, (2) thickness and collagen content of the thin cap covering the core, (3) inflammation within the cap, and (4) cap 'fatigue". Long-term repetitive cyclic stresses may weaken a material and increase its vulnerability to fracture, ultimately leading to sudden and unprovoked (i.e., untriggered) mechanical failure due to fatigue.

Thus, it is one object of the invention to characterize a thin cap of atherosclerotic plaque in an artery of a patient by measuring stiffness of the thin cap, comprising the steps of inserting a catheter into lumen of the artery, configuring and adapting the catheter for advancing and retreating within the lumen by a motorized system controlled by a computer, engaging longitudinal and circumferential movements of the catheter by the motorized system, recording pressure differentials within artery wall by pressure sensors on the catheter, sending data from the pressure sensors to the computer, analyzing the data by a software reconstruction program on the computer, comparing analyzed data to data collected on a reference arterial tissue and determining degree of elasticity of the atherosclerotic plaque to characterize the plaque. The catheter is the disclosed device with its two preferred embodiments.

Atherosclerotic plaque is characterized as intraluminal soft plaque, hard calcified plaque or pre-plaque. Soft plaque is vulnerable plaque characterized by a thin cap with a lipid-rich core beneath the thin cap.

The stiffness of plaque is determined in terms of differential pressures expressed as an elasticity index, defined as a ratio of Young's moduli of the plaque tissue to a reference tissue at a predetermined pressure. The pressure sensor can be a silicone membrane sensor, an ultrasound sensor or a force gauge sensor. Where the sensor is an ultrasound sensor, the ultrasound system emit and receive ultrasound signals. Reference arterial tissue is arterial tissue devoid of atherosclerotic plaque and can be tissue adjacent to the atherosclerotic plaque tissue.

The catheter is the disclosed device with its two preferred embodiments.

In addition, further characterization of plaque is means of measuring plaque temperature and pH respectively with at least one temperature sensor and at least one pH sensor attached to the expandable element of the catheter. The pressure sensors serve as a feedback to ensure tissue wall contact for temperature measurements. The temperature sensor can be a thermocouple sensor, a thermister sensor or an infrared sensor, which comprises an optical fiber.

Further, artery lumen can be measured by width gauges on the shaft of the catheter. Data from the sensors on the expandable element and the width gauges on the shaft are analyzed by a software reconstruction program which creates three-dimensional image maps of the luminal wall.

Where there is a problem in determining if pressure, temperature and pH measurements are indeed those of the tissue wall, pressure, temperature and pH sensors attached to the shaft of the catheter to measure those parameters in the blood. Such measurements are then compared to those taken by sensors in the expandable element.

In another object of the invention, a method for screening stiffness and texture of a biological tissue in a patient for cancer during an interventional procedure is disclosed. The method comprises inserting a catheter into the tissue, configuring and adapting the catheter for advancing and retreating within the tissue by a motorized system controlled by a computer, engaging longitudinal and circumferential movements of the catheter by the motorized system, measuring elasticity of the tissue by pressure sensors on the catheter, sending data from the pressure sensors to the computer, analyzing the data by a software reconstruction program on the computer and comparing analyzed data to data collected on a reference tissue.

Cancer tissue from a body part can be tissue from the prostate, bladder, uterus, nose, mouth, larynx, lung, esophagus, duodenum, rectum and colon. Reference tissue is tissue free of cancer. One example of an interventional procedure is a biopsy procedure.

The stiffness and the texture of tissue is determined in terms of differential pressures expressed as an elasticity index, defined as a ratio of Young's moduli of the tissue to a reference tissue at a predetermined pressure. The pressure sensor can be a silicone membrane sensor, an ultrasound sensor or a force gauge sensor. Where the sensor is an ultrasound sensor, the ultrasound system emit and receive ultrasound signals.

Reference tissue is tissue devoid of cancer.

The catheter is the disclosed device with its two preferred embodiments.

In addition, further characterization of tissue is means of measuring tissue temperature and pH respectively with at least one temperature sensor and at least one pH sensor attached to the expandable element of the catheter. The temperature sensor can be a thermocouple sensor, a thermister sensor or an infrared sensor, which comprises an optical fiber.

Further, the biological tissue can be tissue lining a body cavity. The width of any section of the body cavity can be measured by width gauges on the catheter.

In the case of a biopsy procedure, pressure, temperature and pH are incorporated on the biopsy needle to obtain measurements of those parameters while the needle is approaching the target tissue.

Data from all sensors and width gauges are created by a software reconstruction program that generates three-dimensional image maps of the tissue.

The following references were cited herein:

de Korte et al., Identification of atherosclerotic plaque components with intravascular ultrasound elastography in vivo: a Yucatan pig study. *Circulation* 105(14):1627–30 (2002).

de Korte et al., Morphological and mechanical information of coronary arteries obtained with intravascular elastography; feasibility study in vivo. *Eur Heart J.* 23(5): 405–13 (2002).

Diamantopoulos et al., Intravascular capacitometry: a new method to image both morphology and composition of the coronary wall by using a special intracoronary catheter. *ACC Journal* 37:18A, supplement A (2001).

Diamantopoulos et al., Simultaneous thermal and morphology mapping of the coronary arteries in vivo: a new method to study the atherosclerotic plaque, by means of a special catheter that combines intravascular ultrasounds with thermography. *ACC Journal* 37:4A, supplement A (2001).

Diamantopoulos et al., 3-D thermal reconstruction of the atherosclerotic plaque, a new insight into plaque vulnerability by means of thermography and advanced computer algorithms. *ACC Journal* 37:382A, supplement A (2001).

Fischer et al., Predicting plaque rupture: enhancing diagnosis and clinical decision-making in coronary artery disease. *Vasc Med* 5:163–172 (2000).

Gul et al., Coronary thermosensor basket catheter with thermographic imaging software for thermal detection of vulnerable atherosclerotic plaques. *ACC Journal* 37:18A, supplement A (2001).

Khan et al., pH and lactate imaging of atherosclerotic plaques. *ACC Journal* 37:3A, supplement A (2001).

Naghavi et al., First prototype of a 4 French 180 degree side-viewing infrared fiber optic catheter for thermal imaging of atherosclerotic plaque. *ACC Journal* 37:3A, supplement A (2001).

Naghavi et al., New developments in the detection of vulnerable plaque. *Curr Atheroscler Rep.* 3(2):125–35 (2001).

Naghavi et al., pH Heterogeneity of human and rabbit atherosclerotic plaques; a new insight into detection of vulnerable plaque. *Atherosclerosis.* 164(1):27–35 (2002).

Wang et al., Human serology in Chlamydia tranchomatis infection with microimmunofluorescence. *J. Infect Dis,* 130:388–97 (1994).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Therefore, changes therein, including modifications and alterations, and other uses will occur to those skilled in the art which are encompassed within the spirit of the invention as defined by the scope of the claims or the equivalents thereof.

What is claimed is:

1. A medical device for measuring the stiffness of biological tissue in a patient, comprising:
   (a) a catheter having a proximal end and a distal end;
   (b) a shaft extending through the catheter from the proximal end to the distal end, the shaft comprising a guide wire adapted for moving the catheter in longitudinal and circumferential directions;
   (c) an expandable element connected to the proximal end of the catheter; and
   (d) at least one pressure sensor attached to the expandable element, the pressure sensor being adapted to measure elasticity of organic tissue.

2. The device of claim 1, wherein the pressure sensor is a sensor selected from the group consisting of a silicone membrane sensor, an ultrasound sensor, and a force gauge sensor.

3. The device of claim 2, wherein the ultrasound sensor comprises an ultrasound system that emits and receives ultrasound signals.

4. The device of claim 1, wherein the expandable element is expandable at a deployment step and retractable during an insertion step of the catheter.

5. The device of claim 1, wherein the pressure sensor is adapted to measure pressure when the expandable element contacts a tissue wall.

6. The device of claim 1, wherein the expandable element comprises a plurality of wires in a basket arrangement.

7. The device of claim 6, wherein the pressure sensors attached to the basket arrangement of wires are cantilever sensors.

8. The device of claim 1, wherein the expandable element comprises a plurality of wires in a radial arrangement.

9. The device of claim 8, wherein the pressure sensors attached to the radial arrangement of wires are cantilever sensors.

10. The device of claim 1, wherein the distal end of the catheter is connected to a motorized system for deployment and pullback of the catheter.

11. The device of claim 10, wherein the motorized system is connected to and controlled by a computer and wherein the computer is adapted to analyze data from the sensors on the device with a software reconstruction program.

12. The device of claim 11, wherein the device has at least one temperature sensor and at least one pH sensor attached to the expandable element of the catheter.

13. The device of claim 12, wherein the temperature sensor is selected from the group consisting of a thermocouple sensor, a thermister sensor and an infrared sensor.

14. The device of claim 13, wherein the infrared sensor comprises an optical fiber.

15. The device of claim 12, wherein the device has width gauges attached to the catheter shaft for determining diameter of an artery lumen.

16. The device of claim 15, wherein the software reconstruction program is adapted to create three-dimensional image maps of the lumen using data sent from the width gauges, temperature sensors and pressure sensors.

17. The device of claim 1, wherein the device has at least one pressure sensor, at least one temperature sensor and at least one pH sensor attached to the shaft of the catheter.

18. The device of claim 17, wherein the pressure sensor is adapted to measure blood pressure, the temperature sensor is adapted to measure blood temperature and the pH sensor is adapted to measure blood pH.

19. A method for characterizing a thin cap of atherosclerotic plaque in an artery of a patient by measuring stiffness of the thin cap, comprising:
 (a) inserting a catheter into a lumen of an artery;
 (b) adapting the catheter for advancing and retreating within the lumen by a motorized system controlled by a computer;
 (c) engaging longitudinal and circumferential movements of the catheter by the motorized system;
 (d) recording pressure differentials within an artery wall by pressure sensors on the catheter;
 (e) sending data from the pressure sensors to the computer;
 (f) analyzing the data by a software reconstruction program on the computer;
 (g) comparing analyzed data to data collected on a reference arterial tissue; and
 (h) determining degree of elasticity and texture of the atherosclerotic plaque to characterize the plaque.

20. The method of claim 19 wherein the stiffness of the plaque tissue is measured in terms of differential pressures expressed as an elasticity index, defined as a ratio of Young's moduli of the plaque tissue to a reference tissue at a predetermined pressure.

21. The method of claim 19, wherein the pressure sensor is a sensor selected from the group consisting of a silicone membrane sensor, an ultrasound sensor, and a force gauge sensor.

22. The method of claim 21, wherein the ultrasound sensor comprises an ultrasound system that emits and receives ultrasound signals.

23. The method of claim 19, wherein reference arterial tissue is tissue devoid of atherosclerotic plaque.

24. The method of claim 23, wherein reference arterial tissue is tissue adjacent to atherosclerotic plaque tissue.

25. The method of claim 19, wherein determining the degree of elasticity of the atherosclerotic plaque comprising characterizing the plaque as one type of plaque selected from the group consisting of intraluminal soft plaque, hard calcified plaque and pre-plaque.

26. The method of claim 25, wherein the soft plaque is vulnerable plaque characterized by a thin cap and a lipid-rich core beneath the thin cap.

27. The method of claim 19, wherein the catheter has a proximal end and a distal end, the proximal end has an expandable element, the distal end being connected to the motorized system and a shaft extending through the catheter from the proximal end to the distal end.

28. The method of claim 27, wherein the expandable element comprises a plurality of wires in a basket arrangement and the pressure sensors are attached to the basket arrangement.

29. The method of claim 28, wherein the pressure sensors are cantilever sensors.

30. The method of claim 27, wherein the expandable element of the catheter has a plurality of wires in a radial arrangement and the pressure sensors are attached to the basket arrangement.

31. The method of claim 30, wherein the pressure sensors are cantilever sensors.

32. The method of claim 19, wherein plaque temperature is measured by at least one temperature sensor on the expandable element and plaque pH is measured by at least one pH sensor on the expandable element.

33. The method of claim 32, the pressure sensors on the catheter works as a feedback to ensure contact with tissue wall for temperature measurements.

34. The method of claim 32, wherein the temperature sensor is selected from the group consisting of a thermocouple sensor, a thermister sensor and an infrared sensor.

35. The method of claim 34, wherein said infrared sensor comprises an optical fiber.

36. The method of claim 32, wherein the lumen of the artery is measured by at least one width gauge attached to the catheter shaft.

37. The method of claim 36, wherein the software reconstruction program is adapted to create three-dimensional image maps of the lumen using data sent from the width gauges, temperature sensors and pressure sensors.

38. The method of claim 19, wherein the device has at least one pressure sensor, at least one temperature sensor and at least one pH sensor attached to the shaft of the catheter.

39. The device of claim 38, wherein the pressure sensor is adapted to measure blood pressure, the temperature sensor is adapted to measure blood temperature and the pH sensor is adapted to measure blood pH.

40. A method for screening stiffness of a biological tissue in a patient for cancer during an interventional procedure, comprising:
 (a) inserting a catheter into the tissue;
 (b) configuring and adapting the catheter for advancing and retreating within the tissue by a motorized system controlled by a computer;
 (c) engaging longitudinal and circumferential movements of the catheter by the motorized system;
 (d) measuring elasticity of the tissue by pressure sensors on the catheter;
 (e) sending data from the pressure sensors to the computer;
 (f) analyzing the data by a software reconstruction program on the computer; and
 (g) comparing analyzed data to data collected on a reference tissue.

41. The method of claim 40, wherein the biological tissue is tissue lining a body cavity.

42. The method of claim 40, wherein analyzing is performed to detect cancer from a body part is selected from the group consisting of prostate, bladder, uterus, nose, mouth, larynx, lung, esophagus, duodenum, rectum and colon.

43. The method of claim 40, wherein the reference tissue is tissue free of cancer.

44. The method of claim 40, wherein the interventional procedure is a biopsy procedure.

45. The method of claim 44, wherein pressure sensors and temperature sensors are incorporated on a biopsy needle and adapted to determine temperature and stiffness of a target tissue while approaching the target tissue.

46. The method of claim 44, wherein the pressure sensors and temperature sensors are cantilever sensors.

47. The method of claim 45, wherein the pressure sensors work as a feedback to ensure contact with tissue wall for temperature measurements.

48. The method of claim 45, wherein the software reconstruction program is adapted to create three-dimensional image maps of the tissue wall using data sent from the temperature sensors and pressure sensors.

49. The method of claim 40, wherein the stiffness is measured in terms of differential pressures expressed as an elasticity index, defined as a ratio of Young's moduli of the tissue to a reference tissue at a predetermined pressure.

50. The method of claim 40, wherein the pressure sensor is a sensor selected from the group consisting of a silicone membrane sensor, an ultrasound sensor, and a force gauge sensor.

51. The method of claim 50, wherein the ultrasound sensor comprises an ultrasound system that emits and receives ultrasound signals.

52. The method of claim 40, wherein the catheter has a proximal end and a distal end, the proximal end has an expandable element, the distal end being connected to the motorized system and a shaft extending through the catheter from the proximal end to the distal end.

53. The method of claim 52 wherein the expandable element comprises a plurality of wires in a basket arrangement and the pressure sensors are attached to the basket arrangement of wires.

54. The method of claim 53, wherein the pressure sensors are cantilever sensors.

55. The method of claim 52, wherein the expandable element of the catheter has a plurality of wires in a radial arrangement and the pressure sensors are attached to the radial arrangement of wires.

56. The method of claim 55, wherein the pressure sensors are cantilever sensors.

57. The method of claim 40, wherein biological tissue temperature is measured by at least one temperature sensor on the expandable element and biological tissue pH is measured by at least one pH sensor on the expandable element.

58. The method of claim 57, wherein the pressure sensors on the catheter work as a feedback to ensure contact with tissue wall for temperature measurements.

59. The method of claim 58, wherein the software reconstruction program is adapted to create three-dimensional image maps of the tissue wall using data sent from the temperature sensors and pressure sensors.

60. The method of claim 57, wherein the temperature sensor is selected from the group consisting of a thermocouple sensor, a thermister sensor and an infrared sensor.

61. The method of claim 60, wherein said infrared sensor comprises an optical fiber.

* * * * *